United States Patent [19]

Watts

[11] 4,119,643
[45] Oct. 10, 1978

[54] 4-AMINO-6-NITRO DERIVATIVES OF 2H-3,4-DIHYDROBENZO[b]PYRANS

[75] Inventor: Eric Alfred Watts, Harlow, England

[73] Assignee: Beecham Group Limited, Great Britain

[21] Appl. No.: 753,899

[22] Filed: Dec. 23, 1976

[30] Foreign Application Priority Data

Jan. 27, 1976 [GB] United Kingdom ............... 02994/76

[51] Int. Cl.$^2$ .................... C07D 311/02; A61K 31/35
[52] U.S. Cl. ............................ 260/345.2; 260/239 A; 424/283
[58] Field of Search ...................................... 260/345.2

[56] References Cited

PUBLICATIONS

Watts, Chemical Abstract, 84, 121650e, (1976).

*Primary Examiner*—Nicky Chan
*Attorney, Agent, or Firm*—Jacobs & Jacobs

[57] ABSTRACT

Orally and parenterally administrable compositions for the treatment of hypertension, the active hypotensive agent of which is an aminochromanol or pharmaceutically acceptable acid addition salt thereof. The preparation of the active agent is described.

5 Claims, No Drawings

4-AMINO-6-NITRO DERIVATIVES OF 2H-3,4-DIHYDROBENZO[b]PYRANS

This invention relates to aminochromanols, to their preparation and to compositions containing them.

British Patent Application No. 24348/74, now patent 1,495,526, disclosed the anti-hypertensive efficacy of the compounds of the formula (I):

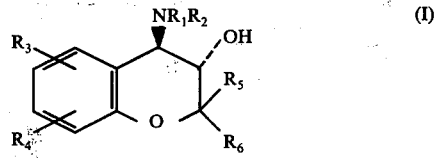

and acid addition salts therof wherein $R_1$ is a hydrogen atom or a $C_{1-9}$ hydrocarbon group optionally substituted by a hydroxyl or $C_{1-6}$ alkoxyl group; $R_2$ is a hydrogen atom or $C_{1-6}$ alkyl group or $NR_1R_2$ is a 3-8 membered heterocyclic group optionally substituted by one or two methyl groups; $R_3$ is a hydrogen or halogen atom or a $C_{1-6}$ alkyl, $C_{2-6}$ alkenyl, $C_{1-6}$ alkoxyl, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_4$, $ASR_7$, $ASO_2R_7$, $ANHR_7$, $ANR_7COR_8$, $ANR_7SO_2R_8$ or $ANR_7CO_2R_8$ group wherein A is an alkylene group of 1-4 carbon atoms; $R_7$ is an alkyl group of 1-4 carbon atoms and $R_8$ is an alkyl group of 1-4 carbon atoms; and $R_4$ is a hydrogen or a halogen atom or $R_3$ together with $R_4$ forms a —CH = CH - CH = CH—, —NH — CH = CH—, —CH$_2$ — CH$_2$ — CH$_2$ — CH$_2$— or —CH$_2$ — CH$_2$CH$_2$ — CO— system; $R_5$ is a hydrogen atom or a $C_{1-6}$ alkyl or phenyl group; and $R_6$ is a hydrogen atom or a $c_{1-6}$ alkyl or phenyl group.

It has now been discovered that a further particularly active group of anti-hypertensive compounds exists.

Accordingly the present invention provides compounds of the formula (II):

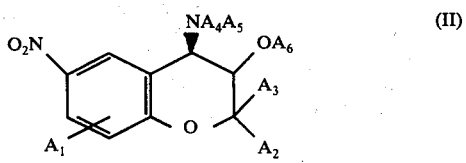

and salts thereof wherein $A_1$ is a hydrogen, fluorine or chlorine atom or a hydroxy, methoxy or methyl group; $A_2$ is a hydrogen atom or a $C_{1-4}$ alkyl group; $A_3$ is a hydrogen atom or a $C_{1-4}$ alkyl group; $A_4$ is a hydrogen atom or a $C_{1-4}$ alkyl group; $A_5$ is a group —X—Y wherein X is an alkylene group of 2 to 6 carbon atoms and Y is a halogen atom or a —OZ group wherein Z is a $C_{1-7}$ hydrocarbon, methanesulphonyl, toluene-p-sulphonyl or phenylsulphonyl; and $A_6$ is a hydrogen atom or a —COA$_7$ group wherein $A_7$ is $C_{1-8}$ hydrocarbon group optionally substituted by halogen or hydroxy.

Suitable $A_1$ is a hydrogen atom.

Suitably $A_2$ and $A_3$ are each methyl or ethyl.

Suitably $A_4$ is hydrogen or methyl.

Suitably $A_5$ is a —(CH$_2$)$_n$Y$_1$ group wherein $n$ is an integer 2 to 5 and $Y_1$ is a halogen atom.

Suitably $A_6$ is a hydrogen atom or acetyl or propionyl group.

Most suitably $A_1$ is a hydrogen atom.

Most suitably $A_2$ is a methyl group.

Most suitably $A_3$ is a methyl group.

Most suitably $A_4$ is a hydrogen atom.

Most suitably $A_5$ is —(CH$_2$)$_n$Cl group where n is an integer 2 to 5.

Most suitably $A_6$ is a hydrogen atom or an acetyl group.

A particularly suitable sub-group of compounds within formula (II) is that of formula (III):

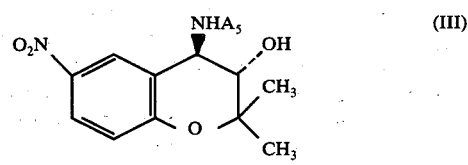

and pharmaceutically acceptable salts thereof, wherein $A_5$ is as defined in relation to formula (II).

Acid addition salts of the amino compounds of formulae (II) - (III) may be made with acids in conventional manner. Suitable salt-forming acids include hydrochloric, hydrobromic, sulphuric, phosphoric, methanesulphonic, p-toluenesulphonic, acetic, propionic, succinic, citric, tartaric, mandelic, lactic, gluconic or other pharmaceutically acceptable organic or inorganic acid.

The compounds of the invention exist in optically active forms. Those skilled in the chemical arts will realise that racemic mixtures of amino compounds can often be separated into pure optical isomers using such techniques as fractional crystallisation, using optically active acids and the like.

A further aspect of this invention provides pharmaceutical compositions suitable for the treatment of hypertension. Such compositions may be suitable for parenteral or oral administration, but in general, oral compositions are preferred because of convenience of administration. Frequently, it is advantageous to administer compounds of the invention together with an adrenergic β-blocking agent and/or a diuretic.

The compositions of this invention are preferably in the form of unit dosage forms such as tablets or capsules. Such unit dosage forms will usually contain from 0.5 to 250 mg., for example, 2 to 100 mg., and will usually be administered from 1 to 6 times a day so that the daily dose for a 70 kg. human is from 2 to 250 mg., for example, 10 to 100 mg.

The compositions of this invention may be formulated in conventional manner, for example, in a manner similar to that used for known antihypertensive agents such as α-methyldopa, propranolol, guanethidine and the like. In conventional manner, the compositions of this invention may contain further active agents such as additional anti-hypertensive agents, diuretics and the like.

From another aspect this invention provides a process for the preparation of compounds of the formula (II) which process comprises:

(a) the reaction of an amine of the formula HNA$_4$A$_5$ with an epoxide of the formula (IV):

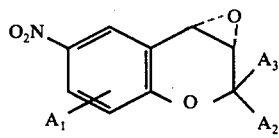

(IV)

wherein $A_1$, $A_2$ and $A_3$ are as defined in relation to formula (II) and therafter, if required, the subsequent conversion of the hydroxy group at the 3-position to a group $OCOA_7$, wherein $A_7$ is as defined in relation to formula (II), by conventional methods or (b) when it is desired to prepare a compound of the formula (II) wherein $A_4$ is a hydrogen atom and $A_5$ is a $-(CH_2)_n Y_1$ group wherein n is an integer from 2 to 6 and $Y_1$ is a halogen atom, the reaction of an acid $HY_1$ with a compound of the formula (V):

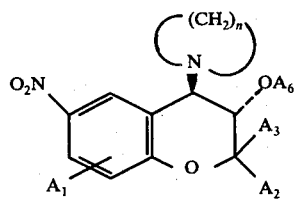

(V)

wherein $A_1$, $A_2$, $A_3$ and $A_6$ are as defined in relation to formula (II).

The reaction of the amine and epoxide may be carried out at any non-extreme temperature (for example $-10°$ C. to 150° C.) and suitably at a temperature between 10° C. and 50° C. (for example at room temperature). The reaction is normally carried out in the presence of an organic solvent that is inert under the reaction conditions used. Suitable solvents include alcohols and ethers (for example aqueous dioxan).

The reaction of the amine and epoxide has been found to give a trans product substantially free from the cis-isomer.

The reaction of the compound of the formula (V) with aqueous acid may be carried out at any non-extreme temperature (for example $-10°$ C. to 150° C.) and suitably at a temperature between 10° C. and 50° C. (for example at room temperature).

It has been found that the compounds of the formula (II) may suitably be isolated in the form of their acid addition salts (for example as their hydrochlorides).

Frequently, pure compounds of this invention prepared by the preceding methods may form crystals which contain water of crystallisation, for example, from 1 to 4 molecules of water per compound of formula (II).

The useful intermediates of the formula (IV) may be prepared by the method described in British Pat. No. 1,495,526 while the useful intermediates of the formula (V) may be prepared from those of the formula (IV) by the reaction of the latter with a heterocyclic amine compound,

wherein n is an integer from 2 to 6 in a suitable solvent such as amyl alcohol.

The following Example illustrates the invention.

EXAMPLE

Trans-4-(3-chloropropylamino)-3,4-dihydro-2,2-dimethyl-6-nitro-2H-benzo[b]pyran-3-ol hydrochloride and methanesulphonate Method (a)

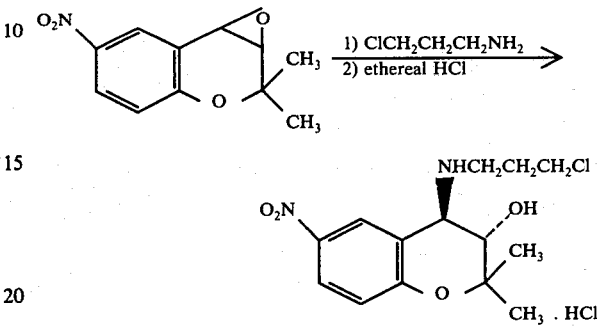

3,4-Epoxy-3,4-dihydro-2,2-dimethyl-6-nitro-2H-benzo[b]pyran (0.50g.), prepared as described in British Pat. No. 1,495,526, chloropropylamine hydrochloride (0.65g.), and sodium hydroxide pellets (0.20g.) in dioxan (25 ml) and water (3 ml) were stirred at room temperature for 6 days. Dilution with water and isolation via ethyl acetate gave a gum (0.62g.) which was separated, by application to silica gel plates and development with ethyl acetate- 60–80° petroleum ether mixture, into starting epoxide (0.34g.) and an amine fraction (0.25g.). The latter was dissolved in diethyl ether and treated with ethereal hydrogen chloride to give trans-4-(3-chloropropylamino)-3,4-dihydro-2,2-dimethyl-6-nitro-2H-benzo[b]-pyran-3-ol hydrochloride (0.15g.); m.p. 242°–243°.

This material was tested by oral administration to groups of six DOCA-salt hypertensive rats and the results were as follows:

| Dose | % age fall in systolic blood pressure | | | |
|---|---|---|---|---|
| | 1 hr. | 2 hr. | 4 hr. | 6 hr. Post-dose |
| 1 mg/kg body wt. | 22 | 24 | 23 | 16 |
| 3 mg/kg body wt. | 35 | 27 | 25 | 31 |
| 10 mg/kg body wt. | 43 | 41 | 38 | 51 |

A larger scale preparation gave an amine fraction (11.30g.) which was dissolved in ethanol (20 ml) and sodium-dried diethyl ether (200 ml) and treated with methanesulphonic acid (3.45g.). After standing in the refrigerator for 60 hours, filtration gave trans-4-(3-chloropropylamino)-3,4-dihydro-2,2-dimethyl-6-nitro-2H-benzo[b]pyran-3-ol methanesulphonate as yellow needles of m.p. 178°–180°.

This material was similarly tested in groups of three DOCA- salt hypertensive rats:

| Dose | % age fall in systolic blood pressure | | | |
|---|---|---|---|---|
| | 1 hr. | 2 hr. | 4 hr. | 6 hr. Post-dose |
| 10 mg/kg body wt. | 28 | 23 | 9 | 0 |
| 30 mg/kg body wt. | 25 | 39 | 13 | 4 |
| 100 mg/kg body wt. | 44 | 42 | 37 | 27 |

Method (b)

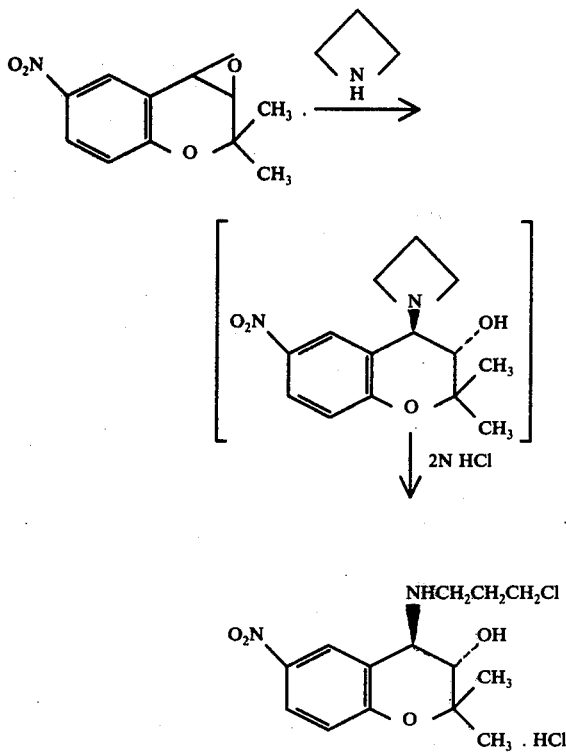

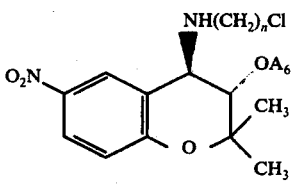

3,4-Epoxy-3,4-dihydro-6-nitro-2H-benzo[b]pyran (1.00g.) was stirred with an approximately 5% solution of azetidine in amyl alcohol (35 ml), prepared by the method of F. C. Schaeffer, J. Amer. Chem. Soc., 5928, 77 (1955), for 29 hours at ambient temperature. Evaporation of solvent left a gum, which on addition of 2N hydrochloric acid gave a yellow precipitate (0.61g.). Two recrystallisations from ethanol-diethyl ether gave the title compound as the hydrochloride salt, m.p. 243°–247°; mixed m.p. 239°–241°.

What is claimed is:

1. A compound selected from the group consisting of a 3,4-dihydrobenzo[b]pyran of the formula:

and a pharmaceutically acceptable acid addition salt thereof, wherein $n$ is an integer of from 2 to 5, and $A_6$ is hydrogen or acetyl.

2. A compound according to claim 1 wherein $A_6$ is hydrogen.

3. A compound according to claim 1 wherein said 3,4-dihydrobenzo[b]pyran is trans 4-(3-chloropropylamino)-2,2-dimethyl-6-nitro-2H-3,4-dihydrobenzo[b]pyran-3-ol.

4. The compound according to claim 1 which is trans 4-(3-chloropropylamino)-2,2-dimethyl-6-nitro-2H-3,4-dihydrobenzo[b]pyran-3-ol hydrochloride.

5. The compound according to claim 1 which is trans 4-(3-chloropropylamino)-2,2-dimethyl-6-nitro-2H-3,4-dihydrobenzo[b]pyran-3-ol methanesulfonate.

* * * * *